United States Patent [19]

Margolis

[11] Patent Number: 5,851,116
[45] Date of Patent: Dec. 22, 1998

[54] INTERPROXIMAL CLEANER AND METHOD OF USE

[76] Inventor: Brian S. Margolis, 43 Grove St., Cold Spring Harbor, N.Y. 11724

[21] Appl. No.: 813,285

[22] Filed: Mar. 10, 1997

Related U.S. Application Data

[60] Provisional application No. 60/013,105 Mar. 11, 1996.

[51] Int. Cl.⁶ ............................. A61C 15/00; A46B 3/18; A46B 9/04
[52] U.S. Cl. ............................. 433/216; 15/106; 15/114; 15/118; 15/167.1; 15/104.94; 15/206; 15/244.1; 15/DIG. 5
[58] Field of Search ............................. 15/104.94, 167.1, 15/206, DIG. 5, 244.1, 106, 114, 118; 132/321, 329; 433/216

[56] References Cited

U.S. PATENT DOCUMENTS

| | | | |
|---|---|---|---|
| D. 291,505 | 8/1987 | Tarrson et al. | D4/104 |
| 3,559,226 | 2/1971 | Burns | 15/167.1 |
| 3,720,975 | 3/1973 | Nelson | 15/167.1 |
| 3,939,520 | 2/1976 | Axelsson | 15/167.1 |
| 4,209,871 | 7/1980 | Ernest et al. | 15/167.1 |
| 4,399,582 | 8/1983 | Ernest et al. | 15/176.4 |
| 4,572,223 | 2/1986 | Rosenfeld | 15/167.1 X |
| 4,911,187 | 3/1990 | Castillo | 132/321 |
| 5,071,348 | 12/1991 | Woog | 433/118 |
| 5,133,971 | 7/1992 | Copelan et al. | 15/244.1 X |
| 5,276,935 | 1/1994 | Lemon et al. | 15/104.94 |
| 5,283,924 | 2/1994 | Kaminski et al. | 15/167.1 X |
| 5,613,258 | 3/1997 | Hilfinger et al. | 15/206 X |

FOREIGN PATENT DOCUMENTS 93-05679   4/1993   WIPO.

*Primary Examiner*—Mark Spisich
*Attorney, Agent, or Firm*—Roberts & Mercanti, L.L.P.

[57] ABSTRACT

The invention is directed in part to an interproximal brush apparatus containing:

a stem portion having a first end and a second end and a longitudinal axis, at least one of said first and said second ends being adapted for receiving an interproximal cleansing portion having an hourglass shape extending 360° along said longitudinal axis of said stem portion. Methods of cleansing interproximal spaces are also disclosed.

11 Claims, 2 Drawing Sheets

INTERPROXIMAL CLEANER AND METHOD OF USE

This application claims the benefit of priority from provisional application Ser. No. 60/013,105 filed Mar. 11, 1996, the contents of which are incorporated herein by reference.

BACKGROUND OF THE INVENTION

1. Field of the Invention

The present invention relates to improvements in dental apparatus. In particular, the present invention is directed to new interproximal cleansing devices and methods of cleansing interproximal regions in mammals.

2. Description of the Prior Art

Over the years, the dental practitioners have stressed the importance of reducing the amount of plaque in the oral cavity. In addition to periodic professional cleaning, patients have been advised to brush frequently, floss on a regular basis and periodically use rinses containing anti-caries or anti-plaque formulations. It is often difficult for patients to keep the interproximal regions, i.e. the region between adjacent teeth, free of plaque. Several devices have been suggested to assist patients in this regard. A sample of such devices is set forth below.

U.S. Pat. No. 3,939,520 discloses a toothbrush having parallel bristles extending in opposite directions from a central plate-like stem. The bristles are all substantially parallel to each other in the width direction of the base plate and extend outwardly from both sides of the attachment plate, i.e., in two straight opposite directions.

U.S. Pat. No. 4,209,871 discloses an hourglass-shaped head for a toothbrush. The bristles of the brush are not in an hourglass shape, but, rather are disclosed as being arranged for interproximal and free gingival margin engagement of both the maxillary and mandibular teeth.

U.S. Pat. No. 4,911,187 discloses a dental pick brush having a plurality of radial bristle elements arranged in a fashion such that relatively short bristles are interposed between longer bristles. Furthermore, the bristles are said to be secured to the shaft and extend outwardly from the shaft in virtually all directions. Although the device is designed for interproximal cleaning, the arrangement of the bristles is not in an hourglass-shape.

In spite of the advances described above, there is still a need for improved interproximal cleaning devices. One of the chief drawbacks associated with currently available devices is that the devices are rather inefficient in cleaning the opposite interproximal embrasure regions simultaneously. Significant amounts of debris, including plaque, are often left on the tooth surfaces after the devices have been utilized with access from one direction. While most devices adequately contact the immediately adjacent surfaces of consecutive teeth, they do not sufficiently clean the tangential tooth surfaces which taper away from the immediately adjacent surfaces, i.e. where the brush protrudes upon insertion. The present invention addresses this shortcoming.

SUMMARY OF THE INVENTION

In accordance with one embodiment of the invention there is provided an interproximal brush apparatus which contains a stem portion having a first end and a second end and a longitudinal axis. At least one of the first and second ends of the stem portion is adapted for receiving an interproximal cleansing portion. The cleansing portion has an hourglass shape which preferably extends 360° about the longitudinal axis of the stem portion.

In accordance with another aspect of the invention, there is provided a method of cleansing interproximal spaces in mammals. The method includes inserting the interproximal cleansing portion of an interproximal brush apparatus, as described above, between adjacent teeth so that the surface of the interproximal cleansing portion of the apparatus contacts and cleans the tooth surfaces which it is in contact with.

One of the advantages of the apparatus of the present invention is the hour-glass shape which uniquely maximizes contact between adjacent teeth without having to physically change directions and angles of insertion. Thus, patient compliance is increased by the design.

DETAILED DESCRIPTION OF THE PREFERRED EMBODIMENT

Figure 1:
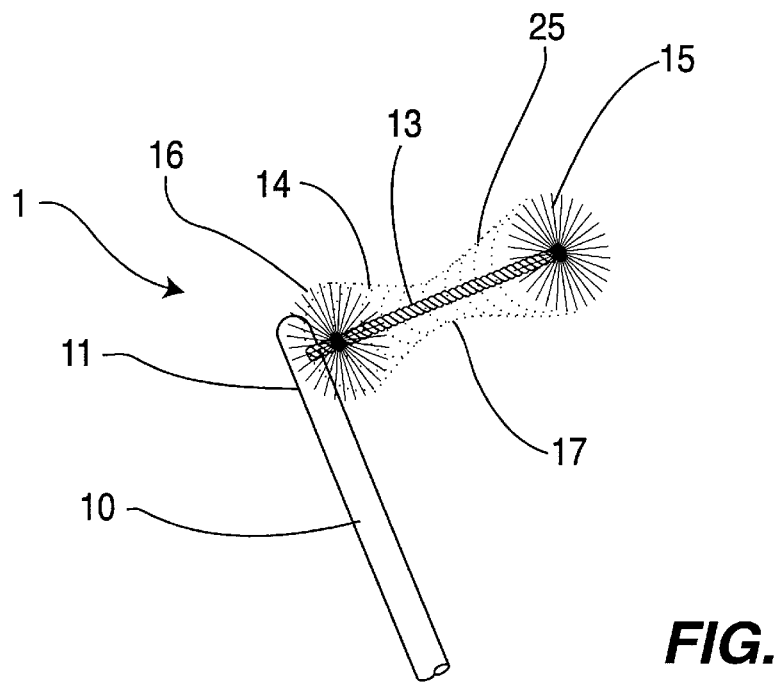
FIG. 1 is a perspective view of a dental apparatus prepared in accordance with the present invention.

In a first aspect of the invention there is provided an improved interproximal brush. Referring now to the Figures, it can be seen that the apparatus 1 includes a stem portion 10 having a first end 11, a second end 12 and a longitudinal axis 13. At least one of the first and second ends is adapted for receiving an interproximal cleansing portion 14 which has a substantially hourglass shape which preferably extends 360° along the longitudinal axis of the stem portion. The cleansing portion 14 is substantially cylindrical in shape and has a first end region 15, a second end region 16 and middle portion 17. The first and the second end regions of the cleansing portion have a greater cross sectional diameter than the middle portion, thus defining a substantially hourglass shape.

Figure 2:
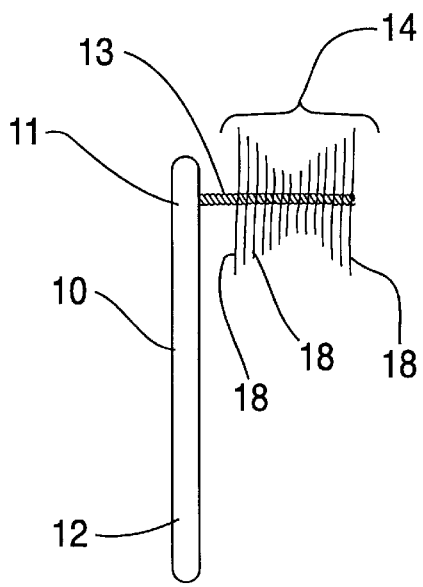
FIG. 2 is a side view of a dental apparatus prepared in accordance with the present invention.
Figure 3:
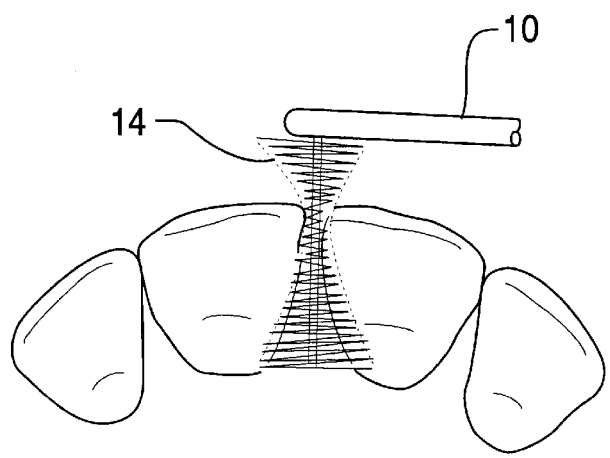
FIG. 3 is a top view of a dental apparatus prepared in accordance with the present invention placed in the interproximal space between adjacent teeth.

The interproximal brush apparatus of the present invention can also be configured so that the interproximal cleansing portion 14 includes a plurality of bristles 18. As can be seen in FIG. 2, the bristles are preferably arranged to extend outwardly from the longitudinal axis 13 and the cleansing portion 14 includes a plurality of bristles 18 which are also arranged in a substantially hourglass shape about the longitudinal axis.

In one embodiment, the interproximal cleansing portion can include a non-bristle based cleaning surface such as a surface having a resilient foam-like material 25. The cleansing portion 14, as shown in FIG. 1, illustrates an orally acceptable polymeric material 25 arranged in a substantially hourglass shape about the longitudinal axis of the stem. In this aspect of the invention, the polymeric material can be designed to include a dentally acceptable abrasive such as a silica-based material bonded to a portion or all of the polymeric surface of the cleansing portion. Alternatively, the polymeric material can be designed to include a dentally acceptable antimicrobial material such as chlorhexidine gluconate releasably bonded to a portion or all of the polymeric surface of the cleansing portion. For example, the polymeric material can include a hydrogel-based system containing an anti-caries or anti-plaque ingredient such as those found in commercially available rinses or foams, i.e. chlorhexidine gluconate, stannous fluoride, sodium fluoride, etc. The ingredient gradually releases from the interproximal cleaner in the interproximal regions for localized treatment in amounts generally regarded as effective treatment dosages. In one embodiment, the interproximal brush apparatus of the present invention is designed so that the interproximal cleansing portion 14 is releasably attached to the stem portion 10 such as by friction or a releasable tab. In this embodiment, the cleansing portions can be removed after use and a sanitary replacement can be attached to the stem upon need. In other aspects of the invention, the apparatus is designed for single use applications and the entire unit is disposed after cleaning one or more interproximal spaces in the oral cavity.

It will be understood that all materials included for the apparatus of the present invention are orally acceptable and can be used in the oral cavity and inserted into the interproximal spaces without causing undesirable side effects i.e. rash, infection, abrasion, etc. For example, the bristles can be prepared from substantially inert polymeric materials such as nylon or similar materials. The stem portion can be stainless steel or coated stainless steel or a suitable plastic resin such as that commonly found on commercially available toothbrushes. It is contemplated that the dental apparatus described herein will include either a flexible or substantially rigid stem portion. Furthermore, it is contemplated that the interproximal cleaning apparatus described herein can be manufactured using currently available injection molding or other acceptable manufacturing techniques and assembly technology.

A still further aspect of the invention includes a method of cleansing interproximal spaces in mammals. This aspect of the invention includes inserting an interproximal brush apparatus as described herein between adjacent teeth so as to allow the cleansing portion 14 to come in contact with and clean the surfaces of the teeth. Thus, the method includes inserting a cleansing apparatus comprising a stem portion having a first end, a second end and a longitudinal axis; at least one of the first and second ends being adapted for receiving an interproximal cleansing portion having an hourglass shape extending 360° along the longitudinal axis of the stem portion. It is contemplated that in preferred aspects of the invention, the methods include using devices containing one or more anti-plaque or antimicrobial agents for local release on/in the cleansing portion of the apparatus.

Figure 4:
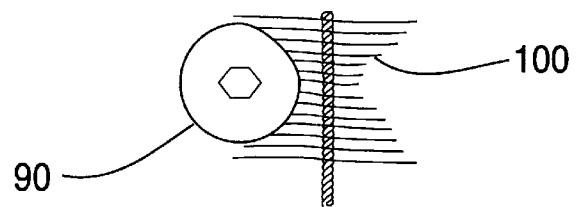
FIG. 4 is a top view of a dental apparatus prepared in accordance with the present invention placed in communication with a transmucosal abutment in the oral cavity.
Figure 5:
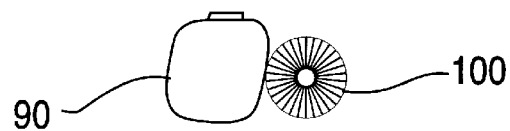
FIG. 5 is a side view of a dental apparatus prepared in accordance with the present invention placed in communication with a transmucosal abutment in the oral cavity.
Figure 6:
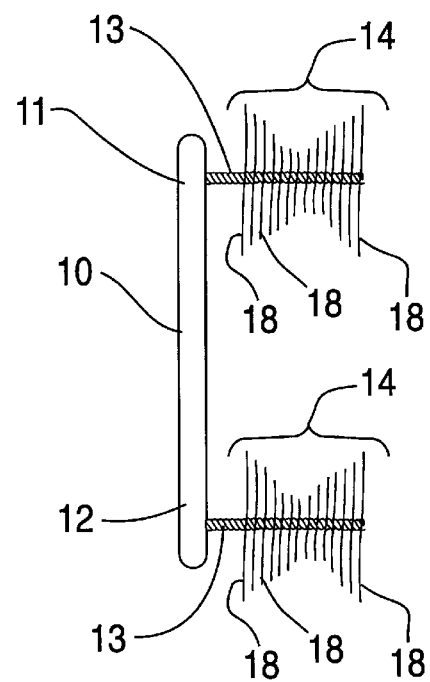
FIG. 6 is a side view of a dental apparatus of the present invention having a cleansing portion on both ends of the stem portion.

A still further embodiment of the invention includes using the apparatus of the present invention to clean around the abutments of dental implants. The hour-glass shape of the cleansing portion allows maximal contact between the device and a transmucosal abutment. Furthermore the shape of the cleansing portion 14 lends itself to gaining improved access to the concave undersurface of an implant suprastructure in a high and dry restoration as such technique is understood by those of ordinary skill in the dental arts. This aspect of the invention is illustrated in FIGS. 4 and 5 with the interproximal apparatus of the present invention designated 100 and the transmucosal abutment designated 90. In this aspect of the invention and those aspects dealing with the method of cleaning interproximal spaces, the stem portion and preferably the cleansing portion are made of non-metallic materials or metallic materials covered with a nylon or other similar material to minimize irritation of the area being treated. Furthermore, the cleansing portion can also be designed to include nylon bristles containing a series of indentations or micropits which serve to better trap and remove debris and/or hold a liquid or gel containing therapeutic ingredient to be delivered to the treated area.

While there have been described what are presently believed to be the preferred embodiments of the invention, those skilled in the art will realize that changes and modifications may be made thereto without departing from the spirit of the invention, and it is intended to claim all such changes and modifications that fall within the true scope of the invention.

I claim:

1. An interproximal brush apparatus comprising:

an elongated stem portion having opposing first and second ends and a longitudinal axis extending between said first and second ends, at least one of said first and second ends releasably receiving an interproximal cleansing portion at a substantially perpendicular angle to the longitudinal axis of said elongated stem; said interproximal cleansing portion having a longitudinal axis and an hourglass shape extending 360° along the longitudinal axis of said interproximal cleansing portion; said interproximal cleansing portion having a continuous resilient foam material surface and a dentally acceptable abrasive.

2. The interproximal brush apparatus of claim 1, wherein said interproximal cleansing portion is releasably attached to said stem portion.

3. The interproximal brush apparatus of claim 1, wherein said first and said second ends of said stem portion are adapted for receiving an interproximal cleansing portion.

4. A method of cleansing interproximal spaces in mammals, comprising:

inserting the interproximal cleansing portion of an interproximal brush apparatus of claim 1 between adjacent teeth whereby debris is dislodged from the interproximal spaces.

5. The interproximal brush apparatus of claim 1, wherein said stem portion is flexible.

6. The interproximal brush apparatus of claim 1, wherein said stem portion is substantially rigid.

7. A dental apparatus, comprising:

a) an elongated stem portion having opposing first and second ends and a longitudinal axis extending between said first and second ends; and b) a head portion releasably affixed to said first end of said stem portion at a substantially perpendicular angle to the longitudinal axis of said elongated stem portion, said head portion having a longitudinal axis, a first end region, a second end region and a middle portion, the first and the second end regions of said head portion having a greater cross sectional diameter than said middle portion, said head portion having a continuous resilient foam material surface and a dentally acceptable anti-plaque or anti-caries compound.

8. The dental apparatus of claim 7, wherein said head portion extends 360° about said longitudinal axis of said head portion.

9. The dental apparatus of claim 7, wherein said head portion comprises an orally acceptable polymeric material arranged in a substantially hour glass shape about said longitudinal axis.

10. The dental apparatus of claim 7, wherein said head portion is removably affixed to said first end of said stem portion.

11. The dental apparatus of claim 7, wherein said second end of said stem portion comprises a handle.

* * * * *